United States Patent
Torii et al.

(10) Patent No.: US 7,931,782 B2
(45) Date of Patent: Apr. 26, 2011

(54) METHOD FOR RECOVERING A LIQUID MEDIUM AND SYSTEM FOR RECOVER A LIQUID MEDIUM

(75) Inventors: Sigeru Torii, Akaiwa (JP); Kouichi Miki, Okayama (JP)

(73) Assignee: The Institute of Creative Chemistry Co., Ltd., Okayama-shi, Okayama (JP)

( * ) Notice: Subject to any disclaimer, the term of this patent is extended or adjusted under 35 U.S.C. 154(b) by 1089 days.

(21) Appl. No.: 10/577,510

(22) PCT Filed: Mar. 26, 2004

(86) PCT No.: PCT/JP2004/004317
§ 371 (c)(1),
(2), (4) Date: Feb. 22, 2007

(87) PCT Pub. No.: WO2005/039725
PCT Pub. Date: May 6, 2005

(65) Prior Publication Data
US 2008/0035467 A1    Feb. 14, 2008

(30) Foreign Application Priority Data

Oct. 29, 2003    (JP) ................. 2003-369166

(51) Int. Cl.
*B01D 1/00* (2006.01)
*B01D 3/10* (2006.01)
*B01D 3/34* (2006.01)
*B01D 3/42* (2006.01)
*B01D 5/00* (2006.01)

(52) U.S. Cl. ......... 201/1; 159/16.1; 159/43.2; 159/47.1; 159/901; 159/DIG. 16; 202/155; 202/160; 202/172; 202/173; 202/185.6; 202/186; 202/205; 203/2; 203/49; 203/78; 203/80; 203/87; 203/94; 203/98; 203/100

(58) Field of Classification Search ................. 159/16.1, 159/27.3, 43.2, 47.1, 901, DIG. 16; 202/155, 202/160, 172, 173, 185.6, 186, 189, 205; 203/1, 2, 49, 78, 80, 87, 94, 98, 100, DIG. 9
See application file for complete search history.

(56) References Cited

U.S. PATENT DOCUMENTS 2,095,578 A * 10/1937 Theiler ........................ 203/49
(Continued)

FOREIGN PATENT DOCUMENTS
FR    2 333 542 A1    7/1977
(Continued)

OTHER PUBLICATIONS

English language translation of the Written Opinion of the International Search Authority Form PCT/ISA/237 (4 pages) mailed Jul. 6, 2006, issued in PCT/JP2004/004317.
(Continued)

*Primary Examiner* — Virginia Manoharan
(74) *Attorney, Agent, or Firm* — Holtz, Holtz, Goodman & Chick PC

(57) ABSTRACT

A method of recovering a liquid medium from a mixture containing the liquid medium, the method including: (a) blowing a first gas into the mixture containing the liquid medium to vaporize the liquid medium, in a first vaporizing means, thereby to form a second gas containing which is a mixture of the first gas and vaporized liquid medium; (b) continuously dropwise feeding the mixture containing the liquid medium into a second vaporizing means and counterflowingly contacting the mixture containing the liquid medium, with the second gas to vaporize additional liquid medium to form a third gas which is a mixture of the second gas and additional vaporized liquid medium; and (c) feeding the third gas into a condensing means to condense the vaporized liquid medium into a liquid and separate the first gas, which is then blown into the first vaporizing means in step (a).

2 Claims, 5 Drawing Sheets

U.S. PATENT DOCUMENTS

| | | | |
|---|---|---|---|
| 3,607,662 A * | 9/1971 | Glover | 202/160 |
| 4,043,875 A * | 8/1977 | Rajakovics et al. | 203/82 |
| 4,245,998 A | 1/1981 | Okouchi et al. | |
| 4,284,480 A | 8/1981 | Sterlini | |
| 4,345,976 A * | 8/1982 | Peter et al. | 203/49 |
| 4,370,949 A * | 2/1983 | Beckett | 122/20 B |
| 4,584,062 A * | 4/1986 | Sussmeyer et al. | 202/197 |
| 4,983,260 A * | 1/1991 | Neel et al. | 203/14 |
| 5,935,388 A * | 8/1999 | Meszaros | 202/155 |
| 6,117,275 A * | 9/2000 | Baumann | 203/1 |
| 6,761,799 B2 * | 7/2004 | Tikka | 162/47 |
| 2002/0062684 A1 | 5/2002 | Holder et al. | |
| 2002/0062794 A1 | 5/2002 | Holder et al. | |

FOREIGN PATENT DOCUMENTS

| | | |
|---|---|---|
| FR | 2 333 544 A2 | 7/1977 |
| JP | 55-102401 A | 8/1980 |
| JP | 59-20802 U | 2/1984 |
| JP | 63-90402 U | 6/1988 |
| JP | 5-285303 A | 11/1993 |
| JP | 08-266803 A | 10/1996 |
| JP | 3046413 U | 12/1997 |
| JP | 2000-185201 A | 7/2000 |
| JP | 2002-143601 A | 5/2002 |
| JP | 2004-113927 A | 4/2004 |

OTHER PUBLICATIONS

An Office Action dated Oct. 20, 2009 in Japanese Appln. 2003-369166 and English translation.

European Search Report for EP 10009575.1 dated Nov. 5, 2010.

European Search Report for EP 10009575.1 dated Nov. 5, 2010.

* cited by examiner

PRIOR ART

PRIOR ART

METHOD FOR RECOVERING A LIQUID MEDIUM AND SYSTEM FOR RECOVER A LIQUID MEDIUM

This application is the United States national phase application of International Application PCT/JP2004/004317 filed Mar. 26, 2004.

FIELD OF THE INVENTION

The present invention relates to a method and a system for separating and recovering a liquid medium from a mixture comprising a liquid medium, such as a solution containing a solute.

The present invention is also concerned with a system for separating and recovering a liquid medium from a solution such as a mixed liquid comprising a liquid medium such as a solvent, and a nonvolatile substance, particularly, a system for separating and recovering the liquid medium while concentrating the mixed liquid.

BACKGROUND ART

In recent years, there is increasing concern about environment problems, and, with respect to the discharge of chemical substances that are possibly harmful to human health and ecosystem, standards, such as ISO, and laws, such as PRTR (pollutant release and transfer register) law, are applied and the regulations are being more strict. For dealing with such movements, recovery of a solvent volatilizing upon, e.g., concentration of a mixed liquid containing a solvent to reduce the amount of the solvent discharged has attracted attention, and, as apparatuses for solvent recovery, recently, a variety of separation apparatuses named, e.g., medium recovery apparatus (solvent recovery apparatus) have come onto the market.

These apparatuses separate a medium based on the principle of distillation under a normal pressure or a reduced pressure (a method in which a solvent is heated to its boiling point to generate saturated vapor and the saturated vapor is separated off), and diagrammatic views of the apparatuses are shown in FIG. 1 and FIG. 2. Reference numerals in the figures designate respective parts as follows: 1: distilling round-bottom flask; 2: heating bath; 3: thermometer; 4: condenser; 5: recovery receiver; 6: coolant connection port; 7: column; 8: solenoid valve; and 9: solenoid valve. FIG. 1 is a generally used simple distillation apparatus for organic solvent, in which solvent vapor formed by boiling a solvent is led to a condenser portion (cooling condenser for condensation 4) where the vapor is condensed and separated. The distillation apparatus of FIG. 2 is an apparatus which separates and purifies a mixed solvent comprising two or more solvents into the individual solvents of single component. In this apparatus, a distilling portion is filled with a solvent, distilling round-bottom flask 1 in the distilling portion is joined to a vertical fractional distillation portion (column tower 7), a condenser portion (cooling condenser for condensation 4) is joined to the upper part of the column, and a branch pipe extends from the condenser portion and is connected to recovery receiver 5. The apparatus has a design such that the branch pipe is further branched before the receiver to achieve reflux of part of the condensate to the upper part of fractional distillation column tower 7, and the recovery and reflux are controlled by solenoid valves 8, 9 and others, thus enabling fractional distillation of solvents. That is, the apparatus purifies a mixed solvent by boiling the organic solvents and appropriately switching the reflux and fractionation.

Japanese Patent Application No. Hei 4-86978 has a description about a method in which used waste liquor comprising n-butanol, butyl acetate, water, 2-butoxyethanol, and 2-hexyloxyethanol is separated by precipitation into an aqueous phase and a solvent phase of high-purity n-butanol and water, and fractionating is repeated under a reduced pressure to recover the solvents. However, in this method, fractionating is achieved by boiling the solvents.

In the above apparatuses, an organic solvent is "distilled" while boiling under a normal pressure or a reduced pressure in principle. For this reason, these apparatuses have the following drawbacks. (1) A solvent vapor pressure is utilized, and hence there is a need to heat a solvent to a temperature equal to or higher than its boiling point. Thus, heating bath 40 for distilling round-bottom flask receiver 26 must be heated to a temperature higher than the boiling point of the solvent. Therefore, when an organic solvent having a low flash point is used, constantly taking care to prevent flaming is indispensable from the viewpoint of achieving safe operations. (2) In the conventional apparatus which is not of a circulation system, the mechanisms of automating the addition of a solvent, the withdrawal of a purified solvent, and the discharge of concentrated mother liquor for continuously operating the apparatus are complicated due to the restrictions by the structure. (3) There are many problems to be solved, e.g., complicated structure of the apparatus and cumbersome operations.

The conventional solvent recovery apparatus comprises, for example, a rotary evaporator which evaporates a solvent under a reduced pressure, a condenser, and a diaphragm pump, and thus is of a system such that a solvent is recovered under a reduced pressure. In the conventional solvent recovery apparatus, when a mixed liquid comprising a solvent is evaporated to recover the solvent, the pressure of the outlet of the recovery portion is reduced using, e.g., a vacuum pump, so that the vaporized solvent moves from the distilling portion into the recovery portion and then into the recovery portion outlet.

However, when the outlet of the recovery portion is under a reduced pressure, the following problems occur. First, the boiling point of the solvent is lowered. In addition, the vacuum pump is difficult to regulate the degree of the reduced pressure, and hence the control of the moving speed of the vaporized solvent, namely, the retention time of the vaporized solvent in the recovery portion is difficult. Therefore, not only does the solvent recovery portion, for example, condenser need a high cooling ability, but also a high solvent concentration is required. Further, there is caused a problem in that a pressure reducing means, e.g., a vacuum pump sucks the vaporized solvent to cause a pump trouble, or leakage of the solvent occurs, for example, the solvent goes out of the apparatus.

Moreover, as apparatuses for use in the purpose of concentration, multi-ingredient sample concentration apparatuses of a system different from the principle of the above-mentioned apparatuses are commercially available as solvent concentration apparatuses. The solvent concentration apparatus is an apparatus in which a mixed liquid comprising a volatile liquid medium, such as a solvent, and a nonvolatile substance (e.g., multi-ingredient sample) is taken in a number of containers, and gas, such as carrier gas, is blown to the contents of all the containers to vaporize the solvent, thus concentrating all of the multi-ingredient samples in short order. This is called multi-ingredient sample concentration apparatus and commercially available. However, in such a solvent concentration apparatus, the vaporized solvent becomes solvent vapor that is released as such to air, together with the carrier gas, and hence the solvent vapor is not recovered. For this reason, a problem of the load on the environment arises and an apparatus which can recover the solvent vapor to be released is strongly desired, but there are the following technical difficulties to be overcome: 1) it is difficult to recover the blown-in carrier gas; 2) it is difficult to recover only the solvent from the dilute solvent vapor contained in the blown-in carrier gas; and 3) an automated apparatus is desired, but a specific method for overcoming the technical difficulties is not found, and hence the fabrication of the apparatus is difficult and such an apparatus has not yet been developed.

It is an object of the present invention to solve the above problems accompanying the conventional apparatuses and provide particularly a novel method and system for "separating and purifying" a solvent without a need to boil the solvent.

It is another object of the present invention to solve the above problems accompanying the conventional apparatuses and provide a novel system for "concentrating" a mixture comprising a liquid medium, such as a solvent, and a non-volatile substance to recover the liquid medium without, discharging the liquid medium into air.

DISCLOSURE OF THE INVENTION

The present invention is directed to a method of recovering a liquid medium which comprises compulsorily contacting the liquid medium with a gas to vaporize the liquid medium, and condensing the vaporized medium.

The present invention is directed to a recovering system of a liquid medium which comprises a vaporizing portion in which a gas is compulsorily contacted with the liquid medium to vaporize the medium, and a condensing portion in which the vaporized medium at the vaporized portion is condensed.

The present invention is directed to a system of a liquid medium which comprises a vaporizing portion in which a gas is compulsorily contacted with the liquid medium to vaporize the liquid medium, a condensing portion in which the vaporized medium at the vaporizing portion is condensed and a separated gas feeding portion in which a separated gas separated by condensation at the condensing portion is fed to the vaporizing portion as a gas to compulsorily contact with the liquid medium.

The present invention is directed to a system of a liquid medium which comprises:

a vaporizing means for vaporizing a liquid medium by contacting a gas to a mixed liquid containing a liquid medium and a non-volatile substance(s), a condensing and separating means for separating the condensed medium and a separated gas by cooling the gas and the vaporized medium fed from the above-mentioned vaporizing means, and a gas feeding means for feeding the separated gas to the vaporizing means as the gas.

BEST MODE FOR CARRYING OUT THE INVENTION

Figure 1:
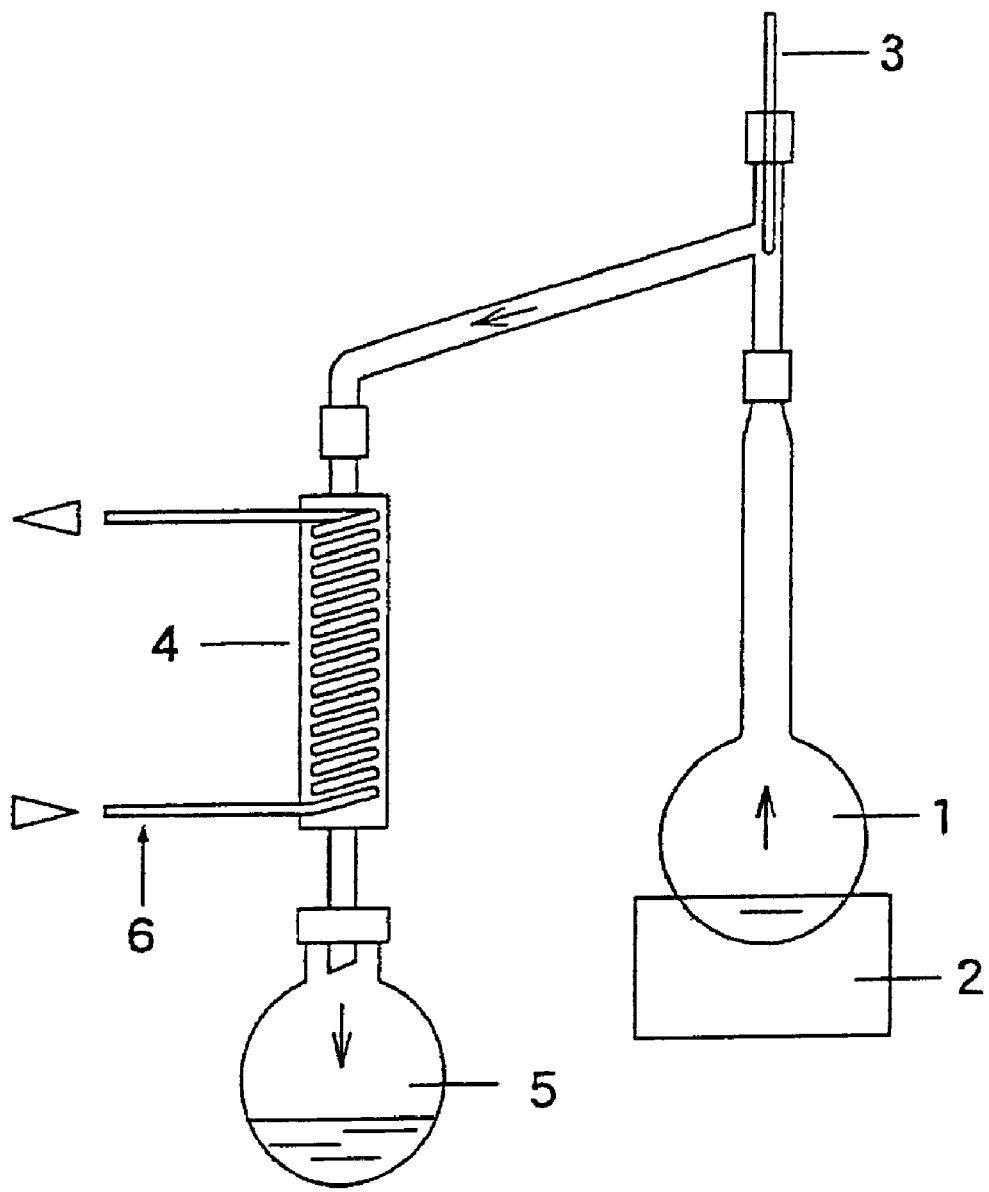
FIG. 1 is a diagrammatic view showing a conventional simple distillation apparatus for organic solvent.
Figure 2:
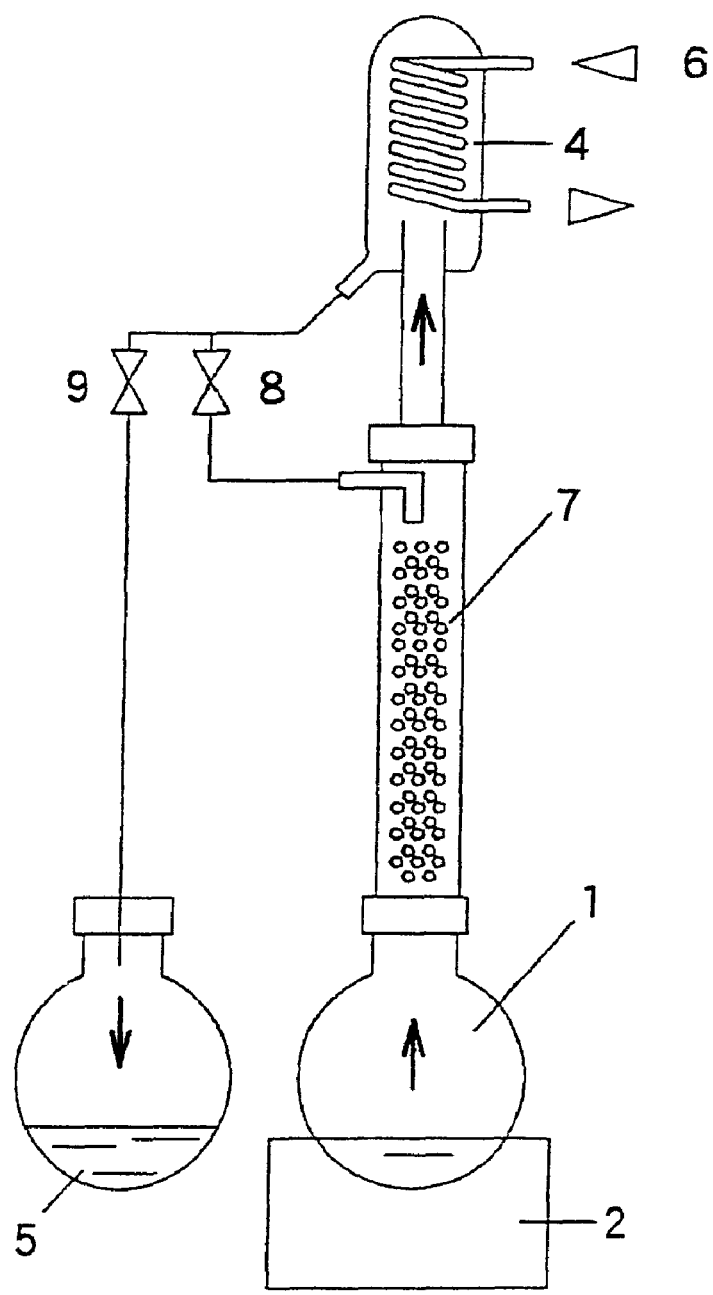
FIG. 2 is a diagrammatic view showing a conventional fractional distillation apparatus for organic solvent.

One embodiment of the present invention is described below.

The present invention (1) is a method for recovering a liquid medium which comprises compulsorily contacting the liquid medium with a gas to vaporize the liquid medium, and condensing the vaporized medium.

The present invention (2) is the recovering method according to the invention (1) above, a gas separated from the medium by condensation is used as the gas to be compulsorily contacted with the liquid medium.

The present invention (3) is the recovering method according to the invention (1) or (2) above, wherein vaporization is carried out at a temperature of the boiling point or lower of the liquid medium when the liquid medium is vaporized.

The present invention (4) is a system of a liquid medium which comprises a vaporizing portion in which a gas is compulsorily contacted with the liquid medium to vaporize the medium, and a condensing portion in which the vaporized medium at the vaporized portion is condensed.

The present invention (5) is a system of a liquid medium which comprises a vaporizing portion in which a gas is compulsorily contacted with the liquid medium to vaporize the liquid medium, a condensing portion in which the vaporized medium at the vaporizing portion is condensed and a separated gas feeding portion in which a separated gas separated by condensation at the condensing portion is fed to the vaporizing portion as a gas to compulsorily contact with the liquid medium.

First, meanings of the terms used in one embodiment of the present invention are described.

With respect to the "liquid medium", there is no particular limitation as long as it is in a liquid state under the conditions for the treatment in the method or system of the present invention, and the liquid medium may be either a single medium or a mixed medium comprised of two or more media, either an organic solvent or an inorganic solvent, or either a polar solvent or a nonpolar solvent. The medium is typically in a liquid state at a normal temperature under a normal pressure. Examples of liquid media include low boiling-point media having a boiling point of 50° C. or lower, such as ether, methylene chloride, and pentane; middle boiling-point media having a boiling point of 50 to 100° C., such as THF, ethyl acetate, chloroform, acetone, hexane, and alcohols, e.g., ethanol and methanol; and high boiling-point media having a boiling point of 100° C. or higher, such as benzene, toluene, DMF, DMSO, and acetonitrile.

The treating liquid medium may be either of a homogeneous system or of a heterogeneous system, e.g., in the state of solution, suspension, or emulsion. As specific examples of the states, there can be mentioned states of the liquid medium which has been used as an extracting agent, a cleaning agent, an elution agent, a developing agent, or an absorbent. Examples of treatments include separation and purification of an extract from crude drugs or the like, and regeneration of an eluent for column chromatography or a cleaning liquid.

With respect to the "gas", there is no particular limitation as long as it is inert to the treating liquid medium and keeps in a gas state even when cooled by a coolant. Gas is appropriately selected depending on the conditions (e.g., vaporizing conditions or condensing conditions) determined according to the treating liquid medium. Specific examples of gas include air, nitrogen, helium, and argon, and preferred is air from the viewpoint of reducing the cost.

The term "gas separated from the medium by condensation" means gas which has passed through the condensing portion. The vaporized liquid medium is mixed with gas, but, when it passes through the condensing portion, the medium is condensed to be a liquid medium and separated from the gas, and hence the separated gas substantially does not contain the medium. Therefore, the partial pressure of the medium is so small that the medium is easily vaporized when the gas was compulsorily contacted with the medium. According to the condensing conditions, the gas may contain the medium in a certain amount.

The expressing reading "gas to be compulsorily contacted with the liquid medium" means changing gas into a gas stream using a pump or the like, and blowing the gas stream against a liquid medium, or bubbling the gas stream into the liquid, namely, mechanically and artificially making a gas-liquid and the gas stream to be compulsorily contacted with a boundary film formed at the interface between the liquid and the gas and to remove the boundary film, thus constantly renewing the boundary film.

Next, various conditions for recovery of the liquid medium in the method or system of the present invention are described. First, with respect to the compulsorily contact, a contact method, for example, a counter-flow, parallel-flow, crossing, or spraying method can be used. In the counter-flow contact, preferred is a method in which the mixture is allowed to fall along and in contact with the sidewall from the upper portion and the gas is passed from the lower part toward the upper part, or a method in which a double-helical tube is heated with an outer tube and the mixture is allowed to flow in an inner tube to wet the wall. Alternatively, the gas can be passed above or blown to the surface of the mixture to be in contact with the mixture. The gas can be passed through the mixture, for example, the gas is bubbled into the mixture. On the other hand, spraying can improve the contact efficiency, but, in this case, it is preferred to spray droplets having such a small size that the droplets do not form a mist.

With respect to the heating, it is preferred that the liquid medium is vaporized at a temperature equal to or lower than the boiling point of the liquid medium. For example, with respect to the high boiling-point or middle boiling-point organic solvent, it is preferred that the bath temperature is adjusted to a temperature lower than the boiling point by 10 to 20° C. On the other hand, with respect to the low boiling-point organic solvent, it is preferred that the bath temperature is adjusted to a temperature lower than the boiling point by 5 to 10° C. The liquid medium may be vaporized at a temperature equal to or higher than the boiling point of the liquid medium.

Next, the condensing conditions may be conditions of temperature such that the vaporized medium is changed to liquid, but, for improving the efficiency, it is preferred to set the condensation temperature for the medium as low as possible.

The condensation temperature for the low boiling-point medium is preferably 0 to −40° C., more preferably −10 to −30° C.

The condensation temperature for the middle boiling-point medium is preferably 10 to −30° C., more preferably 0 to −20° C.

The condensation temperature for the high boiling-point medium is preferably 20 to −20° C., more preferably 10 to −10° C.

As an example of preferred mode of one embodiment of the present invention, there can be mentioned a mode in which the gas is allowed to circulate through a closed system. This mode is advantageous not only in that there is no fear that the medium is released to the outside and it is safe from an environmental point of view, but also in that the circulation of gas keeps the recovery yield high even when the condensation in the condensing portion is insufficient.

Figure 3:
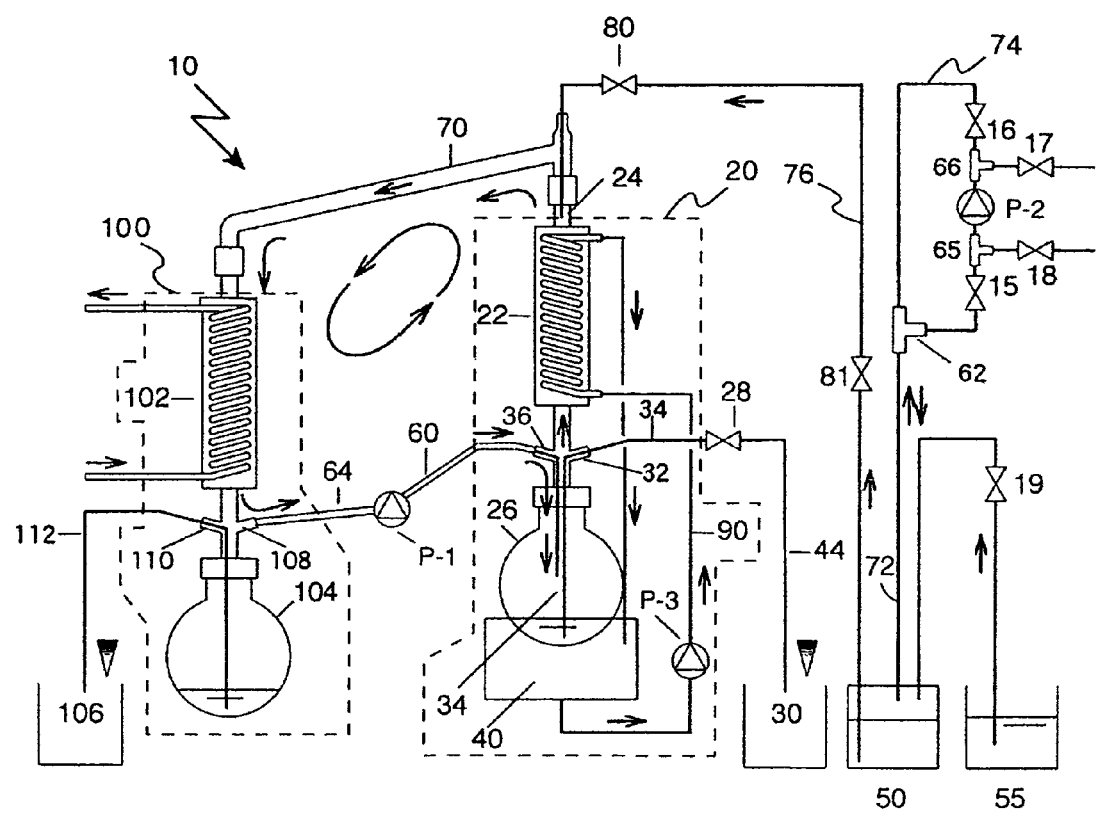
FIG. 3 is a diagrammatic view showing an organic solvent automatic purification system according to one embodiment of the present invention.

A preferred mode of a liquid medium recovery system according to one embodiment of the present invention is shown in FIG. 3.

Representative reference numerals in the figure designate respective parts as follows: 10: liquid medium recovery system; 15: automatic solenoid valve; 16: automatic solenoid valve; 17: automatic solenoid valve; 18: automatic solenoid valve; 19: automatic solenoid valve; 20: vaporizing portion (heating portion, distilling round-bottom flask receiver); 22: heating portion; 24: liquid medium feed inlet, or recovered solvent feed inlet; 26: distilling round-bottom flask receiver; 28: automatic solenoid valve; 30: waste liquor storage tank; 32: branch pipe; 34: connecting conduit; 36: branch pipe; 40: heating bath; 44: connecting conduit; 50: closed tank for solvent feeding; 55: stock solvent tank; 60, 64: connecting conduit (transition tube pipe); 62, 65, 66: three-way branch pipe; 70: connecting conduit (feeding portion); 80: needle on-off valve; 81: automatic solenoid valve; 90: connecting conduit; 100: condensing portion (condenser, round-bottom flask receiver); 102: cooling condenser for condensing; 104: round-bottom flask receiver; 106: purified solvent storage tank; 108: branch pipe; 110: branch pipe; 112: connecting conduit; P-1: diaphragm pump (feeding portion); P-2: pressure-vacuum dual pump; and P-3: heating bath circulation pump.

Liquid medium recovery system 10 comprises heating portion 22 and cooling condenser for condensing 102, and connecting conduits 70, 60, and 64 for connecting the upper part and the lower part in the above portions, and liquid medium recovery system 10 constitutes a closed, cyclic circulation system. Gas circulation diaphragm pump P-1 made of a fluororesin is provided between connecting conduits 60 and 64. Diaphragm pump P-1 makes gas contained in the cyclic circulation system to circulate compulsorily through the system to vaporize and purify the liquid medium fed from liquid medium feed inlet 24 to vaporizing portion 20, so that the medium is condensed in condensing portion 100 and recovered.

With respect to the material used in the system of the present invention, there is no particular limitation as long as the material is impermeable to gas and liquid and has a chemical resistance. Examples of the materials include inorganic materials, such as carbonaceous materials, glass and enamel, stainless steel, and ceramics; organic materials, such as polyethylene, polypropylene, tetrafluoroethylene resins, trifluorochloroethylene resins, vinylidene fluoride resins, ethylene propylene fluoride resins, perfluoroalkoxy resins, unsaturated polyester, epoxy resins, vinyl ester resins, furan resins, and fluororesins; metal materials, such as transition metals, e.g., titanium, noble metals, e.g., Pt, Al—Mg alloys, Cu alloys (e.g., Cu—Sn alloys, Su—Zn alloys, Cu-AL alloys, and Cu—Ni alloys), and Ni alloys (e.g., Ni—Cu alloys, Ni—Mo alloys, and Ni—Cr alloys); composite materials; and materials coated with a corrosion-resistant material. Preferred are glass, fluororesins, and stainless steel.

The pump used for gas circulation may be any pump having a chemical resistance, preferably diaphragm pump P-1 having an inside made of a fluororesin. Diaphragm pump P-1 is used under conditions such that no vapor mist is generated, enabling the gas to slowly circulate through the circulation system.

With respect to the gas transferring ability of diaphragm pump P-1, an ability to make gas in a volume per minute in the range of from 0.1 to 10 times the total internal volume of the liquid medium (organic solvent) automatic purification system to circulate compulsorily is required, but a diaphragm pump having an ability to make gas in a volume per minute in the range of from 0.3 to 3 times the total internal volume of the system to circulate compulsorily is preferably used. For example, when the total internal volume of the organic solvent automatic purification system is 3 to 4 L, a diaphragm pump made of a fluororesin having a displacement rate of 15 to 1 L/min can be used, but a diaphragm pump having a displacement rate of 8 to 3 L/min is preferably used.

An organic solvent is fed dropwise from recovered solvent feed inlet 24 in a conduit made of a fluororesin at the upper part of vaporizing portion 20 which comprises heating portion 22 and distilling round-bottom flask receiver 26, and part of the organic solvent flows down along and in contact with the inner wall of heating portion 22 and arrives at distilling round-bottom flask receiver 26. The organic solvent fed dropwise is warmed and vaporized in vaporizing portion 20 which comprises heating portion 22 and distilling round-bottom flask receiver 26.

Connecting conduit 60 made of a fluororesin is inserted into one branch pipe 36 provided between heating portion 22 and distilling round-bottom flask receiver 26. The distance between the bottom of distilling round-bottom flask receiver 26 and one end of connecting conduit 60 is adjusted depending on the type of the organic solvent, but connecting conduit 60 is preferably fixed so that the distance between the end of connecting conduit 60 and the bottom of distilling round-bottom flask receiver 26 is generally about 4 to 8 cm. Another end of connecting conduit 60 is connected to diaphragm pump P-1. Gasification of the organic solvent is achieved by blowing gas fed by diaphragm pump P-1 from the another end of connecting conduit 60 against the surface of the solvent in distilling round-bottom flask receiver 26. Alternatively, connecting conduit 60 may be positioned so that its end touches the organic solvent in distilling round-bottom flask receiver 26 and gas is bubbled into the organic solvent. Feeding gas into distilling round-bottom flask receiver 26 makes an upward gas stream in heating portion 22, which is a counter flow relative to the organic solvent fed dropwise from recovered solvent feed inlet 24.

Connecting conduit 34 made of a fluororesin is inserted into another branch pipe 32 provided between heating portion 22 and distilling round-bottom flask receiver 26. Connecting conduit 34 is fixed so that the distance between one end of connecting conduit 34 and the bottom of distilling round-bottom flask receiver 26 is about 2 cm. Further, another end of connecting conduit 34 is connected to automatic solenoid valve 28, and the outlet of automatic solenoid valve 28 is connected to waste liquor storage tank 30 through connecting conduit 44. Thus, the residue remaining in distilling round-bottom flask receiver 26 can be transferred from distilling round-bottom flask receiver 26 to waste liquor storage tank 30.

The recovered organic solvent is fed dropwise from recovered solvent feed inlet 24 in the conduit made of a fluororesin at the upper part of vaporizing portion 20, and the dropwise feed rate is controlled by needle on-off valve 80.

One end of conduit 72 is connected to the upper part of closed tank for solvent feeding 50. One end of three-way branch pipe 62 is connected to another end of conduit 72, and conduit 74 is connected to the remaining two ends of three-way branch pipe 62 to form a round of conduit. To conduit 74 are connected automatic solenoid valve 16, three-way branch pipe 66, pressure-vacuum dual pump P-2, three-way branch pipe 65, and automatic solenoid valve 15 in this order. Further, automatic solenoid valve 17 is connected to three-way branch pipe 66, and automatic solenoid valve 18 is connected to three-way branch pipe 65.

One end of conduit 76 is connected to closed tank for solvent feeding 50. Another end of conduit 76 is connected to recovered solvent feed inlet 24 through needle on-off valve 80 and automatic solenoid valve 81.

The starting up of pressure-vacuum dual pump P-2 and the opening or closing operations of automatic solenoid valves 15, 16, 17, 18, 19, 81 and others are controlled with timing preliminarily programmed, so that closed tank for solvent feeding 50 can be under a pressure or a reduced pressure.

The recovered organic solvent is fed to vaporizing portion 20 as follows.

First, automatic solenoid valve 19 is opened and automatic solenoid valve 81 is closed, and closed tank for solvent feeding 50 is vacuumed using pressure-vacuum dual pump P-2, making the recovered organic solvent to transfer from stock solvent tank 55 to closed tank for solvent feeding 50. Then, automatic solenoid valves 15, 17, 19 are closed and automatic solenoid valves 16, 18, 81 are opened, and closed tank for solvent feeding 50 is moderately pressurized using pressure-vacuum dual pump P-2, making the recovered organic solvent to transfer from closed tank for solvent feeding 50 to heating portion 22. Automatic solenoid valves 15, 16, 17, 18, 19, 81 are operated using pressure-vacuum dual pump P-2 with timing preliminarily programmed so that automatic solenoid valves 15, 17, 19 are closed for pressurizing the tank or automatic solenoid valves 16, 18, 81 are closed for vacuuming the tank, thus controlling the pressure or reduced pressure of closed tank for solvent feeding 50.

Pressure-vacuum dual pump P-2, automatic solenoid valve 28, and others can be controlled at predetermined intervals of time using an apparatus in which a time can be set, e.g., a timer. The intervals of time can be appropriately selected depending on predetermined conditions, for example, the amount of the residual solution increased in distilling round-bottom flask receiver 26. For example, the level of the recovered organic solvent in closed tank for solvent feeding 50 is monitored, and the residual solution in distilling round-bottom flask receiver 26 can be automatically transferred using pressure-vacuum dual pump P-2 to external waste liquor storage tank 30.

Heating bath 40 is provided at the lower part of distilling round-bottom flask receiver 26 in vaporizing portion 20, and distilling round-bottom flask receiver 26 is dipped in heating bath 40 and warmed. Heating portion 22 is connected to heating bath 40 through conduit 90. Heating bath circulation pump P-3 is provided at conduit 90, and heating bath circulation pump P-3 makes the heating bath medium contained in heating bath 40, conduit 90, and heating portion 22 to circulate therethrough, thus making it possible to heat heating bath 40 and heating portion 22.

Distilling round-bottom flask receiver 26, heating portion 22, and others are heated to a temperature equal to or lower than the boiling point of the organic solvent fed dropwise from recovered solvent feed inlet 24, and, generally, with respect to the organic solvent having a high boiling point, they are heated to a temperature lower than the boiling point of the solvent by about 10 to 20° C., and, with respect to the organic solvent having a low boiling point, they are heated to a temperature lower than the boiling point of the solvent by about 5 to 10° C., but it is preferred that the temperature is individually selected according to the vaporization properties of the individual organic solvents. Therefore, the temperature of heating bath 40 is desirably adjusted to a temperature lower than the boiling point of the organic solvent to be purified, preferably kept at a temperature lower than the boiling point of the organic solvent by 5 to 20° C.

In another mode of vaporizing portion 20 in the present invention, heating portion 22 may not necessarily have a distilling ability. For example, only a single or a plurality of gas blowing portions, e.g., distilling round-bottom flask receivers 26 are prepared, and, while appropriately heating these gas blowing portions, gas fed from gas circulation diaphragm pump P-1 is blown into the individual gas blowing portions to vaporize the organic solvent, and the gas is collected and led to cooling condenser for condensing 102.

In this case, as the gas blowing portion, there can be used either the above-described distilling round-bottom flask receiver 26 or a plurality of test tubes prepared in a closed box having a form such that gas is blown to the solvent placed in the test tubes, and, with respect to the way of blowing gas, there is no particular limitation as long as gas can be compulsorily contacted with the organic solvent.

The organic solvent is fed dropwise using pressure-vacuum dual pump P-2 from recovered solvent feed inlet 24 at the upper part of heating portion 22. The feed rate of the recovered solvent by pressure-vacuum dual pump P-2 must be controlled depending on the type of the recovered organic solvent, i.e., gasifiability. Further, the feed rate can be more precisely controlled using needle on-off valve 80 made of a fluororesin provided in the organic solvent automatic purification system. It is preferred that the dropwise feed rate is controlled by opening or closing needle on-off valve 80 according to the type of the recovered organic solvent with reference to the values preliminarily examined, and a preferred feed rate is such that a small amount of the solvent flowing down in heating portion 22 is collected in distilling round-bottom flask receiver 26.

The gas vaporized in distilling round-bottom flask receiver 26 is transferred to heating portion 22, and an organic solvent to be vaporized in heating portion 22 is fed into the gas. Heating portion 22 in vaporizing portion 20 and cooling condenser for condensing 102 in condensing portion 100 are connected to each other through connecting conduit 70. The vapor vaporized in vaporizing portion 20 slowly moves to condensing portion 100. A coolant flows through a cooling pipe of cooling condenser for condensing 102 in condensing portion 100, and the vaporized vapor is condensed in cooling condenser for condensing 102. The organic solvent substantially completely condensed in cooling condenser for condensing 102 is recovered in round-bottom flask receiver 104. When a coolant at a temperature in the range of from 0 to −35° C. flows through the cooling pipe of cooling condenser for condensing 102, the coolant vapor can be condensed, but it is more preferred that a coolant at −10° C. or lower flows.

Connecting conduit 64 made of a fluororesin connected to diaphragm pump P-1 is connected to one branch pipe 108 provided between cooling condenser for condensing 102 and round-bottom flask receiver 104. Connecting conduit 60 made of a fluororesin connected to diaphragm pump P-1 is connected to one branch pipe 36 provided between heating portion 22 and distilling round-bottom flask receiver 26, and the gas led from connecting conduit 60 passes through heating portion 22, connecting conduit 70, cooling condenser for condensing 102, and connecting conduit 64 and returns to diaphragm pump P-1, and thus the gas circulates through the closed system.

Connecting conduit 112 is connected to another branch pipe 110 provided between cooling condenser for condensing 102 and round-bottom flask receiver 104, and connecting conduit 112 is introduced to purified solvent storage tank 106. The purified solvent collected in round-bottom flask receiver 104 at the lower part of condensing portion 100 is automatically transferred to purified solvent storage tank 106 when connecting conduit 112 is fixed so that it has a height appropriately controlled.

A construction may be employed such that a three-way branch pipe is provided in a certain part of connecting conduit 64 and a pressure pump and an automatic valve are further connected to the remaining ends of the three-way branch pipe. By opening the automatic valve connected to pressure pump P-4 (not shown) to make a pressurized state by pressure pump P-4, the purified solvent can be automatically transferred from round-bottom flask receiver 104 to purified solvent storage tank 106. In addition, the residue collected in distilling round-bottom flask receiver 26 can be transferred to the external waste liquor storage tank 30.

In the above example, equipment, such as distilling round-bottom flask receiver 26 in which the organic solvent fed dropwise or the residual solution is collected, or round-bottom flask receiver 104 in which the purified solvent is collected, is made of glass, but equipment made of another material, for example, the above-mentioned material used in the system of the present invention may be used, and equipment appropriately selected according to the operation temperature range or the chemical resistance determined depending on the type of the solvent used can be used.

Another embodiment of the present invention is described below.

Another embodiment of the present invention is directed to a system of a liquid medium which comprises:

a vaporizing means for vaporizing a liquid medium by contacting a gas to a mixed liquid containing a liquid medium and a non-volatile substance(s), a condensing and separating means for separating the condensed medium and a separated gas by cooling the gas and the vaporized medium fed from the above-mentioned vaporizing means, and a gas feeding means for feeding the separated gas to the vaporizing means as the gas.

In one other embodiment of the present invention, it is preferred that the condensing and separating means comprises a first condensing means for condensing the vaporized medium by cooling, and a second condensing means for condensing the vaporized medium passed through the first condensing means by further cooling.

In one other embodiment of the present invention, it is preferred that the system further comprises a temperature-maintaining and heating means of the vaporizing means.

In one other embodiment of the present invention, it is preferred that the system further comprises a supplying means for feeding the vaporized medium generated by the vaporizing means to the vaporizing means as the gas.

In one other embodiment of the present invention, it is preferred that the vaporizing means is to vaporize the medium by blowing the gas to the liquid medium and to simultaneously concentrate the mixed liquid containing the liquid medium.

The system according to one other embodiment of the present invention not only is able to concentrate the mixed liquid comprising a liquid medium and a nonvolatile substance in a closed circulation system but also is able to recover the vaporized medium even in a very low concentration. Particularly, the system according to one other embodiment of the present invention has advantages in that the liquid medium can be vaporized at a temperature equal to or lower than the boiling point of the liquid medium, that the gas circulation speed can be made variable, that a means for condensing and separating the vaporized liquid medium can be selected according to the variable retention rate, and that leakage of the liquid medium does not occur.

Figure 4:
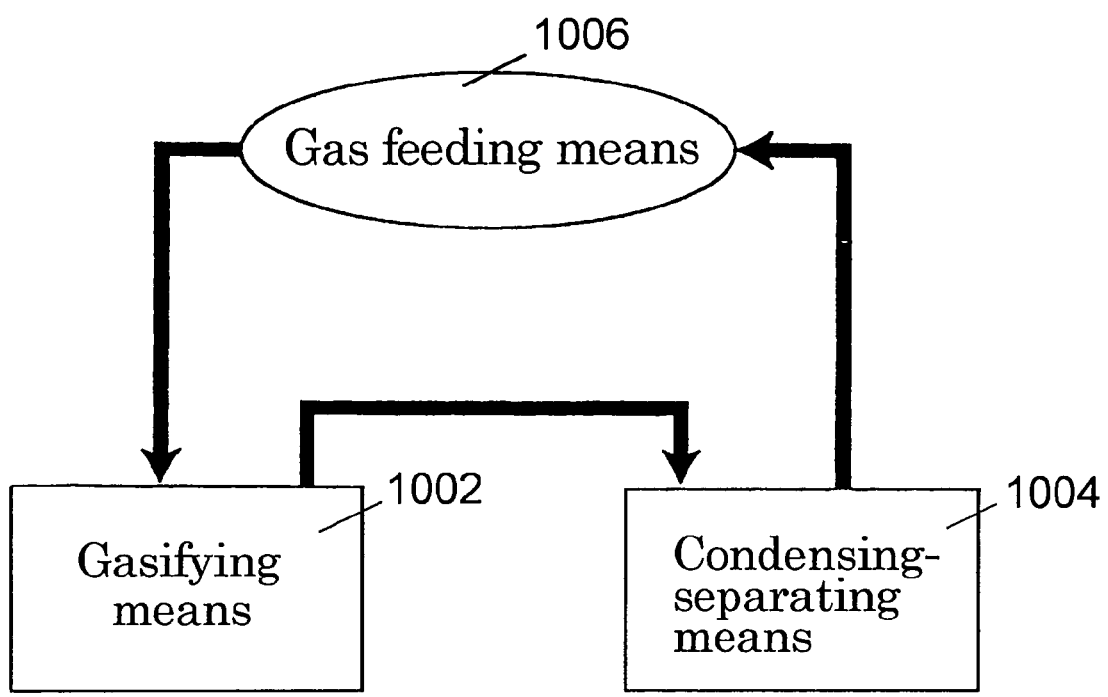
FIG. 4 is a function block diagram showing the function of a system for recovering a liquid medium and concentrating a mixed liquid according to another embodiment of the present invention.

FIG. 4 is a function block diagram showing the function of the system according to one other embodiment of the present invention. Reference numerals in the figure designate respective parts as follows: 1002: vaporizing means; 1004: condensing-separating means; and 1006: gas feeding means.

As shown in FIG. 4, the system according to one other embodiment of the present invention comprises vaporizing means 1002, condensing-separating means 1004, and gas feeding means 1006. In FIG. 4, arrows connecting vaporizing means 1002, condensing-separating means 1004, and gas feeding means 1006 indicate the flow of the gas or medium described below.

Gasifying means 1002 brings gas into contact with a mixed liquid comprising a liquid medium and a nonvolatile substance to vaporize the liquid medium.

Condensing-separating means 1004 cools the gas and the vaporized medium fed from vaporizing means 1002 to separate the condensed medium from the separated gas.

Gas feeding means 1006 feeds the gas separated in condensing-separating means 1004 to vaporizing means 1002 as the gas.

Here the "nonvolatile substance" means a nonvolatile liquid or solid or a mixture thereof present, in liquid phase, together with the liquid medium in a mixed liquid. Specific examples include samples and extracts obtained using the liquid medium as a diluent or an extracting agent.

With respect to the "liquid medium", there is no particular limitation as long as it is in a liquid state and volatile under the conditions for the treatment in the method or system according to another embodiment of the present invention. For example, the liquid medium may be either a single medium or a mixed medium comprised of two or more media, either an organic solvent or an inorganic solvent, or either a polar solvent or a nonpolar solvent. The liquid medium is typically a volatile medium in a liquid state at a normal temperature under a normal pressure (e.g., a solvent). Examples of liquid media include low boiling-point media having a boiling point of 50° C. or lower, such as ether, methylene chloride, and pentane; middle boiling-point media having a boiling point of 50 to 100° C., such as THF, ethyl acetate, chloroform, acetone, hexane, alcohols, e.g., ethanol and methanol, acetonitrile, and benzene; and high boiling-point media having a boiling point of 100° C. or higher, such as toluene, DMF, and DMSO.

The "mixed liquid" may be a mixed liquid which comprises a nonvolatile substance and a liquid medium, and which is either of a homogeneous system, e.g., in the state of suspension or emulsion, or of a heterogeneous system. Specific examples of mixed liquids include mixed liquids being the liquid medium posterior to use as a diluent or as an extracting agent, etc.

With respect to the "gas", there is no particular limitation as long as it is inert to the treating liquid medium and keeps in a gas state even when cooled by a coolant. Gas (e.g., carrier gas) is appropriately selected depending on the conditions (e.g., vaporizing conditions or condensing conditions) determined according to the treating liquid medium. Specific examples of gas include air, nitrogen, helium, argon, and dried gas thereof, and preferred is air from the viewpoint of reducing the cost.

The term "separated gas" means gas which has passed through the condensing-separating means. The liquid medium vaporized (hereinafter, referred to simply as "vaporized medium") is mixed with gas to form mixed gas, but, when it passes through the condensing-separating means, the vaporized medium is condensed to be a liquid medium and separated from the gas, and hence the separated gas essentially does not contain the vaporized medium. Therefore, the partial pressure of the vaporized medium in the separated gas is so small that the medium is easily vaporized when making the gas to be compulsorily contacted with the medium. Depending to the conditions for condensation and separation, the separated gas may contain the vaporized medium to a certain degree, or, depending to the vaporizing conditions, the separated gas may contain the vaporized medium.

Hereinbelow, the above-mentioned vaporizing means 1002, condensing-separating means 1004, and gas feeding means 1006 will be described.

Gasifying Means 1002

As mentioned above, vaporizing means 1002 brings gas (e.g., carrier gas) into contact with a mixed liquid comprising a liquid medium (e.g., a solvent) and a nonvolatile substance to vaporize the liquid medium.

For bringing gas into contact with the mixed liquid, the gas is changed into a gas stream using a pump or the like, and the gas stream is blown to the mixed liquid comprising a nonvolatile substance and a liquid medium, or the gas stream is bubbled into the mixed liquid, namely, a gas-liquid contact is mechanically and artificially made to bring the gas stream into contact with a boundary film formed at the interface between the liquid and the gas and to remove the boundary film, thus constantly renewing the boundary film to vaporize the liquid medium. As a contact method, for example, a counter-flow, parallel-flow, crossing, or spraying contact method can be used. In the counter-flow contact, there can be used a method in which the mixed liquid is allowed to fall along and in contact with the sidewall from the upper portion and the gas is passed from the lower part toward the upper portion, or a method in which a double-helical tube is heated with an outer tube and the mixed liquid is allowed to flow in an inner tube like the wetting-wall tower. It is preferred that the gas is passed above or blown to the surface of the mixed liquid to be in contact with the mixed liquid. The gas can be passed through the mixed liquid, for example, the gas is bubbled into the mixed liquid. On the other hand, spraying can improve the contact efficiency, but, in this case, it is preferred to spray droplets having such a small size that the droplets do not form a mist. It is preferred to blow the gas stream against the mixed liquid comprising a nonvolatile substance and a liquid medium. In vaporizing means 1002, the nonvolatile substance contained in the mixed liquid is not vaporized and only the liquid medium is vaporized, and hence the vaporization of the liquid medium and the concentration of the mixed liquid are conducted simultaneously. Therefore, as vaporizing means 1002 in another embodiment of the present invention, a means generally known as a liquid concentrating means (e.g., concentrating system 1100 shown in FIG. 5 described below) can be used.

Condensing-Separating Means 1004

As mentioned above, condensing-separating means 1004 cools the gas (e.g., carrier gas) and the vaporized medium fed from vaporizing means 1002 to separate the condensed medium from the separated gas.

It is preferred that condensing-separating means 1004 separates all of the vaporized medium from the gas.

As condensing-separating means 1004, a condensing-separating means for separating a part of the vaporized medium from the gas can optionally be added, and, for example, a first condensing-separating means for partially condensing the vaporized medium (first condensing-separating system 1140 shown in FIG. 5 described below) and a second condensing-separating means for completely condensing the vaporized medium (second condensing-separating system 1170 shown in FIG. 5 described below) can be used. In the first condensing-separating means, it is preferred that the vaporized medium is cooled and condensed under a reduced pressure. In the second condensing-separating means, it is preferred that the vaporized medium is further cooled and condensed under an increased pressure. The pressure in the first condensing-separating means can be controlled by changing the gas transfer amount of the mixed gas of the vaporized medium and gas transferred to the second condensing-separating means or the gas transfer amount by the below-described gas feeding means 1006. The pressure in the second condensing-separating means can be controlled by changing the gas transfer amount by the below-described gas feeding means 1006 or the gas transfer amount by the below-described gas supplying means.

The combination of a plurality of partial condensing-separating means and one complete condensing-separating means; the combination of one partial condensing-separating means and a plurality of complete condensing-separating means; or the combinations of one partial condensing-separating means and one complete condensing-separating means arranged in parallel can be used. Particularly, with respect to the low boiling-point medium, it is preferred that a plurality of condensing-separating means are used, and the above-mentioned combination can be used.

Further, the condensing conditions in condensing-separating means 1004 may be conditions of temperature such that the vaporized medium is changed to liquid, but, for improving the efficiency, it is preferred to set the condensation temperature for the medium as low as possible.

The condensing conditions are such that, for example, the temperature is −35 to 20° C.

The condensation temperature for the low boiling-point medium is preferably 0 to −40° C., more preferably −10 to −30° C.

The condensation temperature for the middle boiling-point medium is preferably 10 to −30° C., more preferably 0 to −20° C.

The condensation temperature for the high boiling-point medium is preferably 20 to −20° C., more preferably 10 to −10° C.

With respect to the flow rate of the vaporized medium passing through condensing-separating means 1004, there is no particular limitation, but preferred is a flow rate which does not adversely affect the condensation of the vaporized medium itself.

Gas Feeding Means 1006

As mentioned above, gas feeding means 1006 feeds the separated gas as the gas (e.g., carrier gas) to the above-mentioned vaporizing means 1002.

Gas feeding means 1006 may be any means which makes gas to circulate through the system, and, in the system according to another embodiment of the present invention shown in FIG. 4, gas feeding means 1006 is provided in the route from condensing-separating means 1004 to vaporizing means 1002, but it may be provided in the route from vaporizing means 1002 to condensing-separating means 1004. Further, in the system according to one other embodiment of the present invention, a means for removing the liquid medium obtained in condensing-separating means 1004 may optionally be added.

Further, gas feeding means 1006 may make the vaporized medium transfer along with the gas. The gas feeding can be achieved using, for example, a pump (e.g., first pump 1160 and second pump 1200 shown in FIG. 5 described below).

The gas feeding ability of the pump, i.e., displacement rate is appropriately selected depending on the total volume of the system as mentioned above. As mentioned above, gas feeding means 1006 is provided between vaporizing means 1002 and condensing-separating means 1004, and, preferably, gas is made to circulate in the direction from vaporizing means 1002 to condensing-separating means 1004 and to gas feeding means 1006.

The above-mentioned pump (e.g., first pump 1160 and second pump 1200 shown in FIG. 5 described below) may be any pump having a chemical resistance, preferably a diaphragm pump having an inside made of a fluororesin. A diaphragm pump is used under conditions such that no vapor mist is generated, enabling the gas (e.g., carrier gas) to slowly circulate through the circulation system.

For example, with respect to the gas transferring ability of the pump, an ability to make gas in a volume per minute in the range of from 0.1 to 10 times the total internal volume of medium recovery system 1010 according to another embodiment of the present invention to circulate compulsorily is required, but a pump having an ability to make gas in a volume per minute in the range of from 0.3 to 3 times the total internal volume of the system to circulate compulsorily is preferably used. For example, when the total internal volume of medium recovery system 1010 according to another embodiment of the present invention is 3 to 4 L, a pump made of a fluororesin having a pumping ability of 15 to 1 L/min can be used, but a pump having a pumping ability of 8 to 3 L/min is preferably used.

Hereinbelow, means which can optionally be provided in medium recovery system 1010 according to another embodiment of the present invention, for example, a heating means, a gas supplying means, and a gas cleaning means (not shown) will be described.

Temperature-Keeping and Heating Means

Medium recovery system 1010 according to another embodiment of the present invention can further comprise a heating means. The heating means heats the liquid medium (e.g., a volatile solvent) in the vaporizing means to a temperature equal to or higher than the boiling point of the liquid medium.

In the heating means, for example, with respect to the high boiling-point or middle boiling-point medium, it is preferred that the heating temperature is adjusted to a temperature lower than the boiling point of the medium by 10 to 20° C. On the other hand, with respect to the low boiling-point medium, it is preferred that the heating temperature is adjusted to a temperature lower than the boiling point of the medium by 5 to 10° C. The medium may be heated to a temperature equal to or higher than the boiling point of the medium as long as the object aimed at by another embodiment of the present invention is attained.

For example, for heating the liquid medium to a temperature equal to or lower than the boiling point of the liquid medium, in vaporizing means 1002, the portion for supporting the mixed liquid can be also used as the heating portion (e.g., support 1118 shown in FIG. 5 described below). When vaporizing means 1002 is a closed system, the heating means can be provided outside of that system to heat the entire system.

Gas Supplying Means

Medium recovery system 1010 according to another embodiment of the present invention can further comprise a gas supplying means.

The gas supplying means feeds the vaporized medium (e.g., solvent vapor) generated in vaporizing means 1002 as the gas (e.g., carrier gas) to vaporizing means 1002. For example, mixed gas of the gas and vaporized medium discharged from vaporizing means 1002, or mixed gas of the gas and vaporized medium discharged from the above-mentioned first condensing-separating means 1004 can be fed by the gas supplying means (e.g., a line with a cock or a pump) to vaporizing means 1002.

Further, the gas and vaporized medium discharged from vaporizing means 1002 can be fed by the gas supplying means (e.g., a pump) to condensing-separating means 1004. When there are a plurality of condensing-separating means 1004, gas supplying means are individually disposed between them to feed the gas and vaporized medium.

As examples of pumps for the gas supplying means, there can be mentioned the same examples as those of the pumps for gas feeding means 1006 mentioned above.

Gas Cleaning Means

Medium recovery system 1010 according to another embodiment of the present invention can further comprise a gas cleaning means. The gas cleaning means is a means for removing fine particulate materials, acids, and alkalis (e.g., an adsorption filter or a cleaning trap). The gas cleaning means may be provided in any part of the system according to one other embodiment of the present invention. For example, it is preferred that the gas cleaning means is provided at an outlet (discharge outlet 1116 shown in FIG. 5 described below) of vaporizing means 1002 or at a feed inlet (feed inlet 1114 shown in FIG. 5 described below) through which gas (carrier gas) is fed to vaporizing means 1002.

With respect to the material used in the above-mentioned medium recovery system 1010 according to another embodiment of the present invention, there is no particular limitation as long as the material is impermeable to gas (e.g., carrier gas) and the mixed liquid, and the material has a chemical resistance. Examples of the materials include inorganic materials, such as carbonaceous materials, glass and enamel, stainless steel, and ceramics; organic materials, such as polyethylene, polypropylene, tetrafluoroethylene resins, trifluorochloroethylene resins, vinylidene fluoride resins, ethylene propylene fluoride resins, perfluoroalkoxy resins, unsaturated polyester, epoxy resins, vinyl ester resins, furan resins, and fluororesins; silicon materials, such as silicone resins; metal materials, such as transition metals, e.g., titanium, noble metals, e.g., Pt, Al—Mg alloys, Cu alloys (e.g., Cu—Sn alloys, Sn—Zn alloys, Cu—Al alloys, and Cu—Ni alloys), and Ni alloys (e.g., Ni—Cu alloys, Ni—Mo alloys, and Ni—Cr alloys); composite materials; and materials coated with a corrosion-resistant material. Preferred are glass, fluororesins, and stainless steel.

Medium recovery system 1010 according to another embodiment of the present invention can be used in, for example, the concentration of an extract from crude drugs or the like, or the concentration of a liquid sample; or the recovery of cleaning liquid for machines, parts, boards, or molds.

Hereinbelow, a preferred mode of another embodiment of the present invention will be described in detail with reference to the accompanying drawing.

Figure 5:
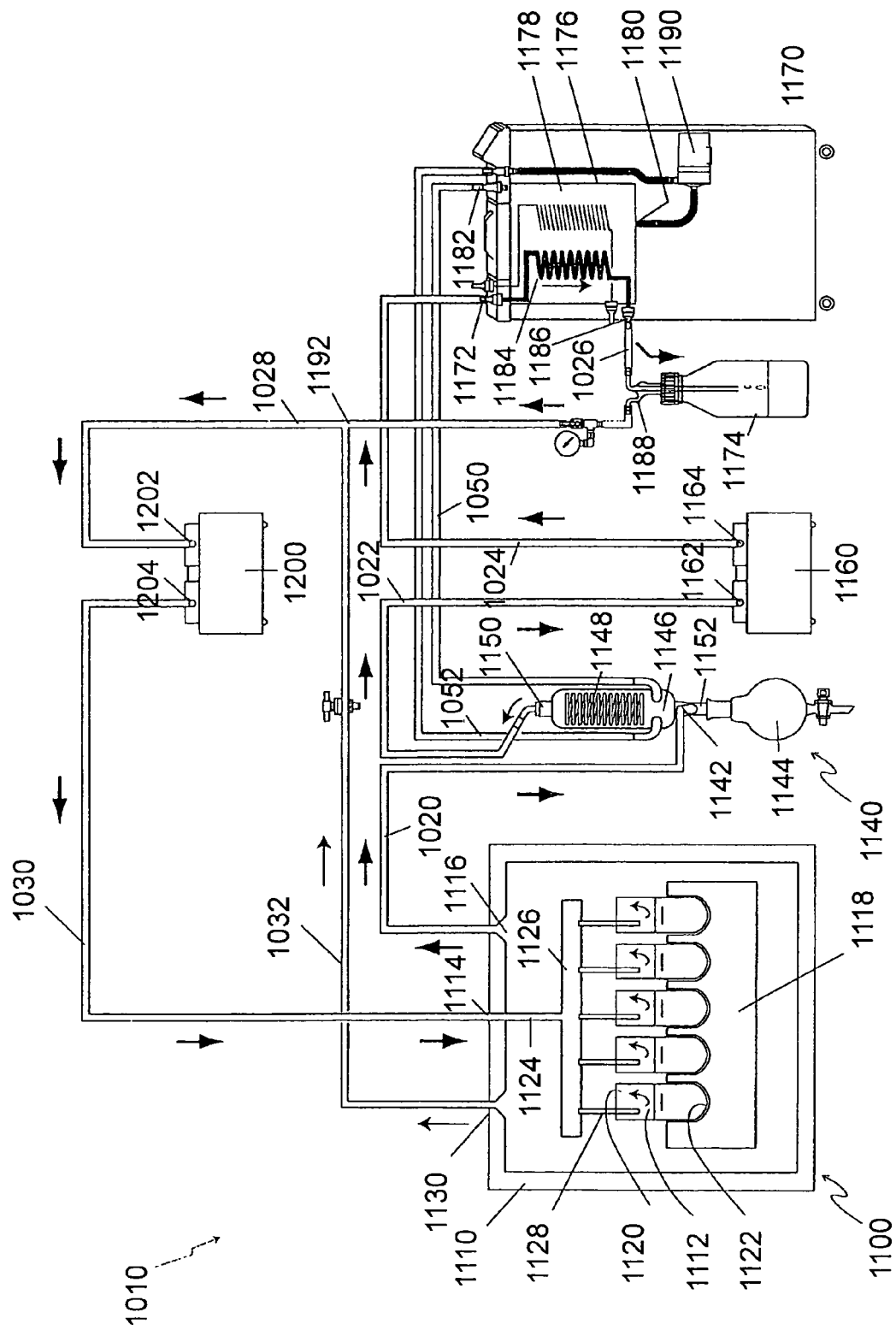
FIG. 5 is a diagrammatic view showing a preferred mode of the system for recovering a liquid medium and concentrating a mixed liquid according to another embodiment of the present invention.

FIG. 5 is a diagrammatic view showing liquid medium recovery system 1010 (system for solvent recovery and multi sample concentration) according to one other embodiment. Representative reference numerals in the figure designate respective parts as follows: 1010: liquid medium recovery system; 1032: supplying pipe (supplying means); 1100: concentrating system (vaporizing means); 1118: support (temperature-keeping and heating means); 1140: first condensing-separating system (first condensing means); 1160: first pump (supplying means); 1170: second condensing-separating system (second condensing means); and 1200: second pump (gas feeding means).

As shown in FIG. 5, liquid medium recovery system 1010 comprises concentrating system 1100, first condensing-separating system 1140, first pump 1160, second condensing-separating system 1170, and second pump 1200.

Concentrating System 1100

Concentrating system 1100 comprises container 1110, and in the upper part of container 1110 are formed feed inlet 1114 through which gas (carrier gas) is fed to container 1110 and discharge outlet 1116 through which the medium vaporized (solvent vapor) in container 1110 is discharged from container 1110. Container 1110 is sealed, excluding feed inlet 1114 and discharge outlet 1116.

Support 1118 for supporting a plurality of multi-ingredient sample containers 1112 is disposed in container 1110. Each multi-ingredient sample container 1112 has a continuous-length shape having opening 1120 at its one end, for example, a test tube-like shape. A multi-ingredient sample can be charged into multi-ingredient sample container 1112 through opening 1120, and the carrier gas fed to container 1110 can be fed through opening 1120 as described below.

Support 1118 is formed from a block comprised of a material which easily conducts heat, for example, aluminum. A plurality of holes 1122 each having a size of shape a little larger than that of multi-ingredient sample container 1112 are formed in the upper surface of support 1118. Multi-ingredient sample containers 1112 are inserted to respective holes 1122, so that multi-ingredient sample containers 1112 can be kept in support 1118. When multi-ingredient sample containers 1112 are inserted to holes 1122, the upper ends of multi-ingredient sample containers 1112 around openings 1120 protrude from support 1118.

A heat source portion (not shown) is connected to support 1118, and heat generated by the heat source portion (not shown) is conducted through support 1118 to individual multi-ingredient sample containers 1112 inserted to holes 1122. A temperature controller (not shown) for controlling the temperature of multi-ingredient sample container 1112 is connected to the heat source portion, making it possible to maintain multi-ingredient sample container 1112 at a desired temperature.

As mentioned above, feed inlet 1114 is formed in the upper part of container 1110. Feed pipe 1124 is connected to feed inlet 1114 so that the pipe extends downwards in the container. Gas branch portion 1126 is provided at the lower end of feed pipe 1124 and supported by a support (not shown). A plurality of nozzle tubes 1128 extending downwards are fitted to gas branch portion 1126. Nozzle tubes 1128 are formed in correspondence with the respective holes 1122 formed in the above-mentioned support 1118. The lower end of each nozzle tube 1128 is opened and the carrier gas fed to feed inlet 1114 can be led downwards through nozzle tubes 1128. When multi-ingredient sample containers 1112 are inserted to holes 1122, the lower ends of nozzle tubes 1128 are individually positioned immediately above the surfaces of the respective multi-ingredient samples charged in multi-ingredient sample containers 1112.

When the carrier gas fed to feed inlet 1114 is introduced through the lower ends of nozzle tubes 1128 positioned immediately above the surfaces of the respective multi-ingredient samples charged in multi-ingredient sample containers 1112, the liquid medium (solvent) contained in the multi-ingredient samples is vaporized to be solvent vapor. As mentioned above, discharge outlet 1116 is formed in the upper part of container 1110, and the solvent vapor is discharged from container 1110 through discharge outlet 1116.

First Condensing-Separating System 1140

One end of pipe 1020 is connected to discharge outlet 1116 formed in the upper part of container 1110. Another end of pipe 1020 is connected to feed inlet 1142 of first condensing-separating system 1140. The solvent vapor discharged from discharge outlet 1116 is fed to first condensing-separating system 1140 through pipe 1020.

First condensing-separating system 1140 comprises storage tank 1144, and condenser 1146 connected to the upper part of storage tank 1144. The above-mentioned feed inlet 1142 is formed around the lower end of condenser 1146. Coolant pipe 1148 having a spiral shape is disposed in condenser 1146. Coolant pipe 1148 has two ends wherein one is connected to coolant feed pipe 1050 and another is connected to coolant discharge pipe 1052. Discharge outlet 1150, through which the carrier gas separated is discharged, is formed in the upper part of condenser 1146. Discharge outlet 1152 through which the solvent separated is discharged is formed in the lower part of condenser 1146. The solvent separated is stored in storage tank 1144 connected to the bottom of condenser 1146.

First Pump 1160

The carrier gas separated is discharged from the above-mentioned discharge outlet 1150 formed in the upper part of condenser 1146. One end of pipe 1022 is connected to discharge outlet 1150. Another end of pipe 1022 is connected to feed inlet 1162 of first pump 1160. Discharge outlet 1164 through which the carrier gas fed is discharged is formed in first pump 1160.

A power source (not shown) for supplying electricity to first pump 1160 is electrically connected to first pump 1160, and, together with the carrier gas fed to feed inlet 1162, the solvent vapor is discharged from discharge outlet 1164 so that the flow rate of the carrier gas discharged from discharge outlet 1164 becomes a desired flow rate.

Second Condensing-Separating System 1170

As mentioned above, together with the solvent vapor, the carrier gas is discharged at a predetermined flow rate from discharge outlet 1164 formed in first pump 1160. One end of pipe 1024 is connected to discharge outlet 1164. Another end of pipe 1024 is connected to feed inlet 1172 of second condensing-separating system 1170. Together with the carrier gas discharged from discharge outlet 1164, the solvent vapor is fed to second condensing-separating system 1170 through pipe 1024.

Second condensing-separating system 1170 comprises storage tank 1174 and cooling condenser for condensing 1176. Coolant tank 1178 for storing a coolant is disposed in cooling condenser for condensing 1176. Coolant tank 1178 has coolant feed inlet 1180 through which a coolant is fed to coolant tank 1178, and coolant discharge outlet 1182 through which the coolant is discharged from coolant tank 1178.

One end of pipe 1184 having a spiral shape is connected to the above-mentioned feed inlet 1172. Another end of pipe 1184 is connected to discharge outlet 1186 formed in the lower part of cooling condenser for condensing 1176. Discharge outlet 1186 is connected to storage tank 1174 through pipe 1026. The solvent condensed in pipe 1184 is fed to storage tank 1174 through pipe 1026.

Discharge outlet 1188 is formed in the upper part of storage tank 1174, and the carrier gas separated from the solvent (hereinafter, referred to simply as "separated carrier gas") by condensing the solvent vapor fed from cooling condenser for condensing 1176 is discharged from discharge outlet 1188. The solvent fed from cooling condenser for condensing 1176 is stored in the lower part of storage tank 1174.

The above-mentioned cooling condenser for condensing 1176 also has circulating pump 1190 for circulating a coolant. Circulating pump 1190 makes both the coolant fed to coolant tank 1178 and the coolant fed to coolant pipe 1148 of condenser 1146 to circulate.

Second Pump 1200

The separated carrier gas is discharged from the above-mentioned discharge outlet 1188 formed in the upper part of storage tank 1174. One end of pipe 1028 is connected to discharge outlet 1188. Another end of pipe 1028 is connected to feed inlet 1202 of second pump 1200. Discharge outlet 1204 through which the carrier gas fed is discharged is formed in second pump 1200.

The carrier gas fed to feed inlet 1202 is discharged from discharge outlet 1204 so that the flow rate of the carrier gas discharged from discharge outlet 1204 of second pump 1200 becomes a desired flow rate.

One end of pipe 1030 is connected to discharge outlet 1204 formed in second pump 1200. Another end of pipe 1030 is connected to feed inlet 1114 of container 1110 in the above-mentioned concentrating system 1100. The carrier gas discharged from second pump 1200 is fed to container 1110 in concentrating system 1100. This construction makes the carrier gas to circulate through the system.

In the above-described construction, vaporizing means 1002 is constituted by concentrating system 1100. Condensing-separating means 1004 is constituted by second condensing-separating system 1170 or first condensing-separating system 1140 and second condensing-separating system 1170. Gas feeding means 1006 is constituted by second pump 1200 or first pump 1160 and second pump 1200.

Further, as shown in FIG. 5, supplying pipe 1032 is provided in medium recovery system 1010.

One end of supplying pipe 1032 is connected to discharge outlet 1130 of container 1110 in concentrating system 1100, and another end of supplying pipe 1032 is connected to feed inlet 1192 provided in a certain part of pipe 1028. By virtue of this structure, the solvent vapor vaporized in container 1110 can be returned to concentrating system 1100 without passing through first condensing-separating system 1140, first pump 1160, and second condensing-separating system 1170, thus making it possible to control the pressure in second condensing-separating system 1170 and the pressure in concentrating system 1100. A flow rate control apparatus, such as a cock, is provided in a certain part of supplying pipe 1032. By virtue of this, the flow rate of the solvent vapor returned to concentrating system 1100 can be controlled, making it possible to regulate the partial pressure of the solvent vapor in concentrating system 1100.

EXAMPLES

Hereinbelow, one embodiment of the present invention will be described in more detail with reference to the following Examples, which should not be construed as limiting the scope of the embodiment of the present invention.

Example 1

In liquid medium recovery system 10 according to one embodiment of the present invention shown in FIG. 3, 100 mL of an ethanol-containing material, which had been used as an eluent for chromatography, was led to closed tank for solvent feeding 50, and the recovered organic solvent was fed dropwise to the closed system from recovered solvent feed inlet 24 using pressure-vacuum dual pump P-2 at a feed rate of 34 mL/min. Diaphragm pump P-1 was controlled so that the gas (air) flow rate became 6 L/min, and the gas was passed through conduit 60 (outer diameter: 6 mm; inner diameter: 4 mm), and conduit 60 was arranged so that the tip of conduit 60 fixed by branch pipe 36 was positioned 6 cm above the bottom of distilling round-bottom flask receiver 26 having a capacity of 1 L. The gas was blown through conduit 60 obliquely against the surface of the recovered organic solvent so that a depressed round area about 2 to 4 mm in depth was formed in the surface of 3 to 4 cm of the recovered organic solvent collected in distilling round-bottom flask receiver 26. The gas blown to the bottom of distilling round-bottom flask receiver 26 moved upwards in the flask, together with the vaporized ethanol, and then arrived at heating portion 22. Heating portion 22 has a straight-pipe distilling portion (inner diameter: 60 mm; length: about 200 mm), and a spiral pipe comprised of a pipe having an outer diameter of 8 mm disposed in the distilling portion, wherein the spiral pipe has a helix outer diameter of 55 mm. A heating bath medium was fed from heating bath 40 into the pipe of the spiral pipe by means of heating bath circulation pump P-3, and the heating bath medium was made to circulate between heating bath 40 and heating portion 22 comprising the spiral pipe to keep heating bath 40 and heating portion 22 at 65° C. Thus, the recovered solvent fed dropwise from recovered solvent feed inlet 24 moved downwards along and in contact with the outer surface of the spiral pipe and the inner wall of the straight-pipe distilling portion in heating portion 22, and brought to contact with the gas flowing upwards in the heating portion, so that part of the recovered solvent was vaporized. The ethanol vaporized in both the distilling round-bottom flask receiver and heating portion 22 passed through connecting conduit 70 and then arrived at cooling condenser for condensing 102 where the ethanol was cooled and condensed into liquid, so that the ethanol liquid was gradually collected in round-bottom flask receiver 104 having a capacity of 1 L. Under the above conditions, almost all the ethanol (>99%) was recovered in round-bottom flask receiver 104 at a rate of about 8.5 mL/min.

Example 2

Substantially the same procedure as in Example 1 was conducted except that, as shown in Table 1, the heating bath temperature was changed from 65° C. to 76° C., the recovered solvent feed rate was changed from 34 mL/min to 5.0 mL/min, and the pump P-1 flow rate was changed from 6 L/min to 30 L/min. The results are shown in Table 1.

Example 3

Substantially the same procedure as in Example 1 was conducted except that, as shown in Table 1, the organic solvent to be recovered was changed from ethanol to methanol, the heating bath temperature was changed from 65° C. to 54° C., and the recovered solvent feed rate was changed from 34 mL/min to 6.8 mL/min. The results are shown in Table 1.

Example 4

Substantially the same procedure as in Example 1 was conducted except that, as shown in Table 1, the organic solvent to be recovered was changed from ethanol to ethyl acetate, the heating bath temperature was changed from 65° C. to 76° C., and the recovered solvent feed rate was changed from 34 mL/min to 10.0 mL/min. The results are shown in Table 1.

Example 5

Substantially the same procedure as in Example 1 was conducted except that, as shown in Table 1, the organic solvent to be recovered was changed from ethanol to chloroform, the heating bath temperature was changed from 65° C. to 54° C., and the recovered solvent feed rate was changed from 34 mL/min to 10.0 mL/min. The results are shown in Table 1.

TABLE 1

| Example | Type of organic solvent recovered | Heating bath (° C.) | Recovered solvent feed rate (mL/min) | Pump P-1 flow rate (mL/min) | Organic solvent recovery flow rate (mL/min) | Organic solvent recovery (%) |
|---|---|---|---|---|---|---|
| 1 | Ethanol | 65 | 34.0 | 6 | 8.5 | >99 |
| 2 | Ethanol | 76 | 5.0 | 30 | 5.0 | >99 |
| 3 | Methanol | 54 | 6.8 | 6 | 5.6 | >99 |
| 4 | Ethyl acetate | 76 | 10.0 | 6 | 5.6 | >99 |
| 5 | Chloroform | 54 | 10.0 | 6 | 7.7 | >99 |

Note: 100 mL of the liquid medium was introduced to closed tank for solvent feeding 50, and then the recovery operation was started.

INDUSTRIAL APPLICABILITY

In an aspect of the present invention, there are provided a method and a system which can purify a solvent under advantageous operation conditions such that the solvent is not boiled.

In another aspect of the present invention, there is provided a system which can "concentrate" a mixture comprising a liquid medium, such as a solvent, and a nonvolatile substance to recover the liquid medium without discharging the liquid medium into air.

The invention claimed is:
1. A method of recovering a liquid medium from a mixture containing the liquid medium, the method comprising:
   contacting the mixture comprising the liquid medium with a first gas to vaporize the liquid medium in a vaporizing means and thereby to form a second gas which is a mixture of the first gas and vaporized liquid medium, and feeding the second gas into a condensing means to condense the vaporized liquid medium and separate the first gas;
   using the first gas separated from the liquid medium by condensation as the first gas to be contacted with the liquid medium; and
   regulating the partial pressure of the vaporized liquid medium in the vaporizing means by a partial pressure regulating means; wherein
   the condensing of the second gas in the condensing means comprises partially condensing the vaporized liquid medium in a first condensing means, and further cooling and completely condensing the vaporized liquid medium in a second condensing means; and
   returning a part of the first gas and the vaporized liquid medium discharged from the vaporizing means through a conduit means in the partial pressure regulating means to the vaporizing means while flowing together with the separated first gas without passing through the first condensing means and the second condensing means and regulating the partial pressure of the vaporized liquid medium by controlling the flow rate of the vaporized liquid medium returning to the vaporizing means through the conduit means, wherein the recovery of the liquid medium is carried out where the first gas is circulated through a closed system under reduced pressure; or vaporization is carried out at a temperature of the boiling point or lower of the liquid medium when the liquid medium is vaporized; or the recovery of the liquid medium is carried out where the first gas is circulated through a closed system under reduced pressure and vaporization is carried out at a temperature of the boiling point or lower of the liquid medium when the liquid medium is vaporized.

2. A liquid medium recovering device for recovering a liquid medium from a mixture containing the liquid medium, the device comprising:

a first vaporizing means which receives a first gas from a blowing means, said first vaporizing means being operable to vaporize the liquid medium to form a vaporized medium, thereby to form a second gas which is a mixture of the first gas and vaporized liquid medium;

a first conduit means communicating with the first vaporizing means and a second vaporizing means, the second vaporizing means comprising a double-helical pipe having a straight-pipe distilling section and a spiral pipe disposed in the straight-pipe distilling section, and being operable to receive the second gas from the first conduit means to a lower part of the straight pipe distilling section, and allow the second gas to flow towards an upper part of the straight pipe distilling section in counter-flow contact with said mixture flowing down said outer surface of the double helical pipe, said second vaporizing means being operable to vaporize additional liquid medium to form a third gas which is a mixture of the second gas and additional vaporized liquid medium;

a second conduit means communicating with the second vaporizing means and with a third condensing means;

the third gas condensing means being operable to condense the vaporized liquid medium in the third gas delivered from the second conduit means, thereby to separate the first gas; and a third conduit means operable to supply the first gas, separated in the third gas condensing means, to said blowing means.

* * * * *